United States Patent [19]

Wallshein

[11] 4,178,687
[45] Dec. 18, 1979

[54] CLAMP, PARTICULARLY FOR ORTHODONTIA

[76] Inventor: Melvin Wallshein, 8645 Bay Pkwy., Brooklyn, N.Y. 11214

[21] Appl. No.: 772,595

[22] Filed: Feb. 28, 1977

[51] Int. Cl.² ............................................. A61C 7/00
[52] U.S. Cl. .................................. 433/13; 339/244 B;
339/249 B; 24/136 B; 151/2 A; 85/1 L
[58] Field of Search ................... 32/14 A; 339/244 B,
339/249 B, 272 B; 24/243 E, 136 B; 151/2 A;
85/77, 83, 1 L; 403/398, 399, 396, 395

[56] References Cited

U.S. PATENT DOCUMENTS

| | | | |
|---|---|---|---|
| 2,027,415 | 1/1936 | Blackburn | 339/244 B |
| 2,546,395 | 3/1951 | Hubbard | 339/244 B |
| 3,028,671 | 4/1962 | Berger | 32/14 A |
| 3,164,900 | 1/1965 | Wallshein | 32/14 A |
| 3,210,818 | 10/1965 | Wallshein | 32/14 A |
| 3,266,364 | 8/1966 | Becker | 85/77 |

FOREIGN PATENT DOCUMENTS

| | | | |
|---|---|---|---|
| 333097 | 10/1958 | Switzerland | 403/396 |
| 794517 | 5/1958 | United Kingdom | 403/399 |

*Primary Examiner*—Russell R. Kinsey
*Assistant Examiner*—John J. Wilson
*Attorney, Agent, or Firm*—Flynn & Frishauf

[57] ABSTRACT

A clamp, particularly suitable for orthodontia, comprises a threaded screw member and a threaded nut member which is threadably engageable therewith. The screw member has a notch thereacross to receive a wire therethrough, the notch being directed generally towards one end of the thread on the screw. The notch opens on a surface of the screw for accepting a wire and has a first portion adjacent the opening which is defined by substantially parallel opposing walls, and has a second bottom portion which is adjacent the first portion and remote from the opening, the second bottom portion being generally V- or U-shaped and defined by inclined walls which are directed toward each other and toward the bottom of the notch. The screw member has a resilient quality so that when one of the screw and nut members is turned relative to each other so that the nut member intercepts a wire positioned through the slot, the wire is forced deeper into the second inclined portion of the notch so that the angle of inclination of the notch walls is increased, the wire is clamped by the members and the nut member is locked on the screw member.

15 Claims, 10 Drawing Figures

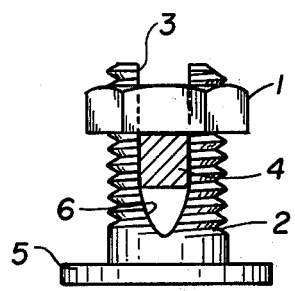
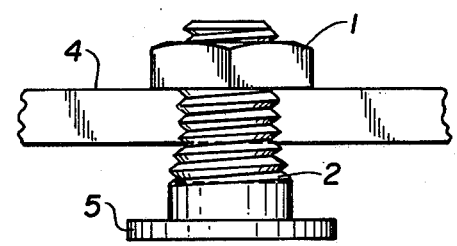
FIG.1  FIG.2
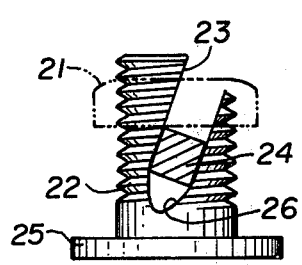
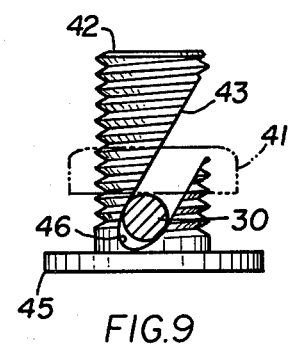
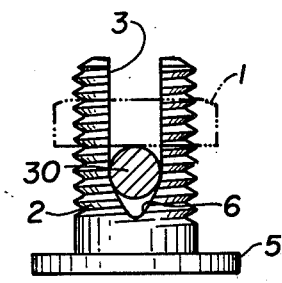
FIG.3  FIG.9  FIG.4
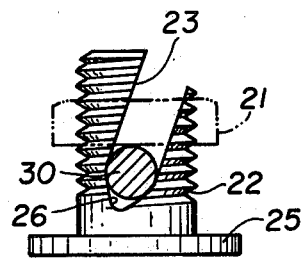
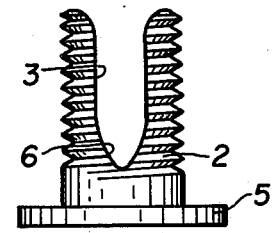
FIG.5  FIG.10  FIG.6
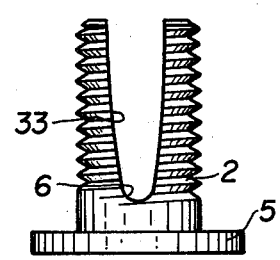
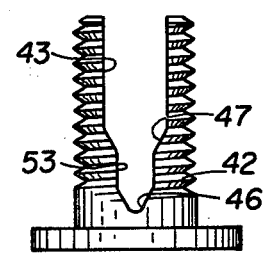
FIG.7  FIG.8

CLAMP, PARTICULARLY FOR ORTHODONTIA

This invention relates to clamps for holding a wire, and more particularly to a clamp particularly suited for use in the practice of orthodontia.

Various types of clamps for clamping a wire in the field of orthodontia exist. A typical clamp is shown, for example, in my prior U.S. Pat. No. 3,210,818, which clamp is difficult to use with orthodontic wires having rectangular cross-section. It is difficult to maintain the proper orientation of a wire having a rectangular cross-section in a generally V-shaped slot or groove since the rectangular cross-section wire can tilt in various orientations in the V-shaped slot or groove.

Another known clamp is that illustrated in U.S. Pat. No. 2,959,856. This clamp requires a specially designed nut member which bites into an orthodontic wire. This has the disadvantage of involving increased costs of production of the clamp (due to the special nut) and weakening of the orthodontic wire where it bites into same.

The object of the present invention is to provide an improved wire-engaging clamp which is particularly suitable for use in the practice of orthodontia and which overcomes the disadvantages of the prior art clamps discussed hereinabove.

It is a further object of the present invention to provide a wire-engaging clamp which is simple and inexpensive to manufacture.

SUMMARY OF THE INVENTION

In accordance with the present invention, a clamping device comprises a threaded screw member and a threaded nut member which is threadably engageable thereon. A notch is provided in the screw member to receive a wire therethrough, the depthwise direction into the notch being at least generally towards one end of the thread on the screw. The notch opens on a surface of the screw and has a first portion adjacent the opening which is defined by substantially parallel opposing walls, and has a second bottom portion adjacent the first portion and remote from the opening, the second bottom portion being generally V- or U-shaped and defined by inclined walls which are directed toward each other and toward the bottom of the notch. The screw member has a resilient quality whereby on turning at least one of the screw and nut members relative to the other so that a wire positioned through the notch is intercepted by the nut member and then forced deeper into the second portion of the notch, the angle of inclination of the inclined notch walls is increased, the wire is clamped by the members and the nut member is locked on the screw member.

The device of the present invention is particularly useful with wires having substantially rectangular cross-sections, but is also useful with wires having round or other cross-sectional shapes which have dimensions so that the wire abuts against the inclined walls of the bottom portion of the notch to increase the angle of inclination of the inclined walls when the nut member is threaded tightly on the screw member.

The notch may open at an end of the screw which is generally substantially perpendicular to the lengthwise direction of the screw or it may open at a threaded portion of the screw member intermediate the ends of the screw member.

BRIEF DESCRIPTION OF THE DRAWINGS

FIG. 1 is an end view of an embodiment of the present invention in use clamping a wire having a rectangular cross-section;

FIG. 2 is a side view of the embodiment of FIG. 1;

FIG. 3 is an end view of another embodiment of the present invention in use clamping a wire having a rectangular cross-section;

FIG. 4 is an end view of an embodiment similar to that of FIG. 1 but clamping a wire having a round cross-section;

FIG. 5 is an end view of an embodiment similar to that of FIG. 3 but shown clamping a wire having a round cross-section;

FIG. 6 is an end view of an embodiment modified from that of FIG. 1;

FIG. 7 is an end view of a still further embodiment of the present invention;

FIG. 8 is a view of a still further embodiment of the present invention;

FIG. 9 is a view of a still further modified embodiment of the present invention; and FIG. 10 is an end view of an embodiment similar to that of FIG. 1.

DETAILED DESCRIPTION OF ILLUSTRATED EMBODIMENTS

Referring to FIGS. 1 and 2, a nut 1 is threadably engaged on a screw 2, which has a notch, groove, or slot 3 cut through an end thereof and which is adapted to receive a wire 4 therein. The wire 4 shown in FIG. 1 is an elongated wire having a generally rectangular cross-section and which is to be clamped in fixed relationship relative to the screw 2. The screw 2 has a head or flange portion 5 which can be secured to, for example, an orthodontic band by welding or any other suitable method, for example as illustrated and discussed in my prior U.S. Pat. No. 3,210,818. The notch or slot 3 is bottomed in a generally V-shaped or U-shaped groove portion 6 having tapered side walls which are downwardly inclined toward each other.

As shown in FIG. 1, a generally rectangular cross-sectional wire 4 is inserted into the notch or slot 3. As the wire 4 enters and proceeds into slot 3, the substantially parallel side walls of the slot 3 guide the rectangular wire 4 into position with a predetermined orientation relative to the screw 2. The substantially parallel side walls of slot 3 restrain the wire 4 so that substantially no tipping or other rotational movement of the wire 4 about its longitudinal axis occurs. As the wire proceeds downwardly deeper into the slot 3, it begins abutting against the inclined surfaces of the lower generally V-shaped portion 6. As the nut 1 is tightened on the screw 2 to press the wire 4 deeper into the slot 3, the lower edges of the wire bear against the inclined surfaces of the V-shaped portion 6 so as to urge the slotted side walls of the upper portion of the screw (as seen in FIG. 1) outwardly toward the mating threaded surfaces of the nut 1, thereby more tightly locking the nut 1 relative to the screw 2. The further downward the wire is pressed into slot portion 6, the tighter the locking between the screw 2 and nut 1 becomes. Thus, by the combination of the locking of the screw 2 relative to the nut 1, and the pressing downward of the wire 4 into the notch, extremely tight binding between the screw and the nut is achieved to prevent accidental loosening, and extremely tight gripping of the wire in the slot 3 relative to the nut 1 and screw 2 is also achieved. FIG. 10 shows a screw with a more pointed V-shaped portion 6'.

FIG. 3 illustrates a modified embodiment of the present invention wherein a slot 23 is formed in an inclined manner with its entrance partly in a side wall and partly in the end wall of a screw 22. A nut 21 is threadably engaged on the screw 22 in order to lock a wire 24 in the slot 23, with the lower portion of the wire bearing against a generally V-shaped lower slot portion 26. As discussed above with respect to the embodiment of FIG. 1, as the nut 21 is tightened downward against the rectangular cross-sectional wire 24, the wire is caused to bottom further in the slot 23 to abut the inclined walls of the lower generally V-shaped portion 26 to urge the side walls of the slot apart relative to each other. This causes the portions of the screw 22 on opposite sides of the slot 23 to be urged apart so that they more tightly engage the nut 21, thereby providing a locking action against accidental movement of the nut 21 relative to the screw 22.

FIGS. 4 and 5 show embodiments of the invention similar to those of FIGS. 1 and 3, respectively, but illustrate use with a generally round cross-sectional wire 30. In FIGS. 4 and 5, similar elements are shown with the same reference numerals as those used in FIGS. 1 and 3, respectively. As shown in FIGS. 4 and 5, as the nut is tightened downwardly against the wire 30, the portions of the screw defining the opposing sides of the slot are urged outwardly relative to each other so as to cause the respective nut to more tightly engage the threaded portions of the screw to provide a locking action against accidental loosening of the nut on the screw.

The above-described arrangements provide a universal locking device which is suitable for use not only with generally round cross-sectional orthodontic wires, but which is also highly desirable for use with generally rectangular cross-sectional orthodontic wires. The device is not only of relatively simple construction which may be inexpensively mass-produced, but also provides extremely secure locking and self-alignment of rectangular orthodontic wires when inserted therein. Different sized slots may be provided for different size rectangular cross-sectional wires in order to provide proper guidance of the respective sized wires in the slots. Since the bottom portions of the slots are generally V-shaped, a single clamp may readily accept many sizes of round orthodontic wires and still operate as desired with the wire abutting the inclined surfaces of the generally V-shaped lower slot portion.

Preferably, the bottom-most portion of the slots 6,26 are rounded as illustrated in the drawing, but other configurations having the desired mutually inclined surface portions at the bottom of the slot may be used. Also, if desired, a nut having a tapered internal thread may be used to provide even further tightening action of the nut relative to the screw. Alternatively, the nut may be normally threaded and the external threads on the screw may be tapered to enhance tightening relative to the nut.

FIG. 6 illustrates a further modification of the present invention wherein the uppermost portions of the walls defining slot 3 have tapered edges so as to facilitate insertion of a rectangular cross-section wire in the slot 3. Other than the upper tapered edges, the remaining elements of the embodiment of FIG. 6 are substantially identical to those of FIG. 1 and like reference numerals are used throughout.

FIG. 7 illustrates another embodiment of the present invention wherein the walls of the slot 33 are just slightly outwardly tapered. This embodiment permits easy entry of a wire having a rectangular cross-section and moreover permits the locking device to be used with rectangular wires having slightly varying cross-sectional dimensions. While the side walls of the slot portion 33 are slightly outwardly tapered, they are still "substantially parallel" within the meaning of the present inventive concept since they are not inclined relative to each other to a degree large enough to permit any substantial tilting or rotation of the rectangular cross-sectional wire about its longitudinal axis. In FIG. 7, the slightly tapered slot portion is designated by reference numeral 33, the remaining elements of FIG. 7 being identical with those of FIG. 1.

While the modifications shown in FIGS. 6 and 7 are with respect to the embodiment shown in FIG. 1, similar modifications may be applied to the embodiment of FIG. 3.

FIG. 8 illustrates a further modification of the invention having a slot or groove with two substantially parallel-walled sections 43, 53 formed in a screw 42. The spacing between the opposing walls of slot section 43 is greater than the spacing between the opposing walls of lower slot section 53. An inclined section 47 is provided between the parallel-walled slot sections 43 and 53. Slot section 53 is bottomed in a generally V-shaped section 46 which is similar in shape and effect to slot section 6 of FIG. 1. If a rectangular cross-sectional wire having a dimension which corresponds substantially to the spacing between opposing walls of slot section 43 is inserted into the slot section 43, the lower ends of the wire will bear against the inclined walls of slot section 47 upon tightening of a nut 1 on the screw 42. If a smaller wire having a dimension corresponding to the spacing between walls of slot section 53 is inserted, the wire will bottom on the inclined surfaces of portion 46 of the slot upon tightening of a nut 1 on screw 46, similar to the action achieved in the embodiment of FIG. 1. The embodiment of FIG. 8 will also accept round cross-sectional wires, as should be apparent. Thus, as a nut is tightened on screw 42, in a manner similar to the tightening in FIG. 1, the screw will be caused to expand by virtue of the pressing of a wire against inclined surfaces 47 or inclined surfaces 46, in a manner similar to that described above with respect to FIGS. 1-7. The modification of FIG. 8 will also accept round wires, as should be apparent, and may also be implemented in a manner similar to FIG. 3.

FIG. 9 illustrates an embodiment similar to that of FIGS. 3 and 5, except that the inclined slot 43 is formed with its entrance solely in the side walls of the screw 42. Otherwise, the embodiment of FIG. 9 is substantially identical to that of FIGS. 3 and 5 in operation and generally in resultant effects. Similar reference numerals are used in FIGS. 3, 5 and 9, except that in FIG. 9, the reference numerals are in the forties.

Typical sizes for wires for use in the present invention are, for example:
round: about 0.014 to about 0.045 inches in diameter
rectangular: about 0.018×0.020 to about 0.022×0.028 inches Wires of other sizes may, of course, be used as required.

While the invention has been described with respect to specific embodiments, various modifications and alterations may be made within the scope of the invention as defined in the appended claims.

I claim:

1. In combination with a rectangular orthodontic wire of given rectangular cross-sectional dimension, an orthodontic clamping device for clamping said rectangular orthodontic wire comprising:
    a screw member having an external thread thereon;
    a nut member having an internal thread which is threadably engageable with the external thread of said screw member;
    said screw member having a notch thereacross to receive said rectangular orthodontic wire therethrough, the depthwise direction into said notch being at least generally towards one end of the thread on said screw member, said notch opening on a surface of said screw and having a first portion adjacent said opening which is defined by substantially flat and substantially parallel opposing walls which are spaced apart to receive said rectangular orthodontic wire therebetween with opposite flat surfaces of said rectangular orthodontic wire adjacent respective opposing substantially flat walls of said notch so that said wire is substantially non-rotational in said notch about the longitudinal axis of said wire, and said notch having a second bottom portion adjacent said first portion and remote from said opening, said second portion being generally V- or U-shaped and defined by inclined walls which are directed toward each other and toward the bottom of said notch, the inclination of said inclined walls of said second portion of said notch being such that said rectangular orthodontic wire when received in said second portion is intercepted by said inclined walls near the portion where said inclined walls meet said opposing substantially flat walls; and
    said screw member being threaded along its length at least to a position substantially where said bottom portion of said notch begins, and having a resilient quality whereby on turning at least one of said screw and nut members relative to the other so that said rectangular orthodontic wire positioned through said notch is intercepted by said nut member and then forced deeper into said second portion of said notch, the angle of said inclined notch walls is increased, the wire is clamped by said members and said nut member is locked on said screw member.

2. A clamping device according to claim 1 wherein the bottom of said second portion of said notch is generally rounded.

3. A clamping device according to claim 1 wherein said notch opens on an end surface of said screw member, said end surface being substantially perpendicular to the longitudinal axis of said screw member.

4. A clamping device according to claim 1 wherein said notch opens at a threaded portion of said screw member intermediate the ends of said screw member.

5. A clamping device according to claim 4 wherein said notch is inclined relative to the longitudinal axis of said screw member.

6. A clamping device according to claim 1 wherein the opposing walls defining said first portion of said notch are outwardly tapered at the portions immediately adjacent the opening of said notch to facilitate insertion of a wire into said notch.

7. A clamping device according to claim 1 wherein said substantially parallel walls defining said first portion of said notch are slightly tapered outwardly toward said opening.

8. A clamping device according to claim 1 further comprising means coupled to said screw member for securing said screw member to a tooth.

9. A clamping device according to claim 1 further comprising means coupled to said screw member for securing said screw member to an orthodontic appliance.

10. A clamping device according to claim 1 wherein said walls defining said second bottom portion of said notch are substantially flat in a direction perpendicular to the depthwise direction of said notch.

11. A clamping device according to claim 1 wherein said screw member is threaded along its length at least to a position substantially at the bottom of said notch.

12. A clamping device according to claim 1 wherein said inclined walls of said second portion of said notch are inclined such that a wire received in said second portion is intercepted by said inclined walls at an intermediate portion of said inclined walls with a space remaining between the wire and the bottom of said notch.

13. In combination with a rectangular orthodontic wire of given rectangular cross-sectional dimension, an orthodontic clamping device for clamping said rectangular orthodontic wire comprising:
    a screw member having an external thread thereon;
    a nut member having an internal thread which is threadably engageable with the external thread of said screw member;
    said screw member having a notch thereacross to receive said rectangular orthodontic wire therethrough, the depthwise direction into said notch being at least generally towards one end of the thread on said screw member, said notch opening on a surface of said screw, said notch having:
    a first portion adjacent said opening which is defined by substantially flat and substantially parallel opposing walls which are spaced apart to receive said rectangular orthodontic wire therebetween;
    a second bottom portion remote from said opening and defining the bottom of said notch, said second portion being generally V- or U-shaped and defined by inclined walls which are directed toward each other and toward the bottom of said notch, the inclination of said inclined walls of said second portion of said notch being such that said rectangular orthodontic wire when received in said second portion is intercepted by said inclined walls near the upper portion of said inclined walls;
    a third portion immediately adjacent said second bottom portion, said third portion being defined by substantially parallel opposing walls which are spaced apart a distance less than the spacing between the substantially parallel opposing walls of said first portion of said notch; and
    a fourth portion between said first and third portions, said fourth portion being defined by inclined walls which are directed toward each other and toward the bottom of said notch and connecting the walls of said first and third portions; and
    said screw member being threaded along its length at least to a position substantially where said bottom portion of said notch begins, and having a resilient quality whereby on turning at least one of said screw and nut members relative to the other so that said rectangular orthodontic wire positioned through said notch is intercepted by said nut member and then forced deeper into said notch, the angle of the inclined notch walls engaged by said wire is increased, the wire is clamped by said members and said nut member is locked on said screw member; whereby a rectangular orthodontic wire having a dimension corresponding to the distance between the opposing walls of said first portion is caused to bear upon the inclined walls of said fourth portion to increase the angle of inclination of the walls of said fourth portion when intercepted and forced by the nut member deeper into said notch, and a rectangular orthodontic wire having a dimension corresponding to the spacing between the opposing walls of said third section is caused to bear against the inclined surfaces of said second bottom portion to increase the angle of inclination thereof when said wire is intercepted by said nut member and forced deeper into said second portion of said notch.

14. A clamping device according to claim 13 wherein said walls defining said second, third and fourth portions of said notch are substantially flat in a direction perpendicular to the depthwise direction of said notch.

15. An orthodontic clamping device for clamping an orthodontic wire of given cross-sectional dimension, comprising:

a screw member having an external thread thereon;

a nut member having an internal thread which is threadably engageable with the external thread of said screw member;

said screw member having a notch thereacross to receive a wire therethrough, the depthwise direction into said notch being at least generally towards one end of the thread on said screw member, said notch opening on a surface of said screw, said notch having:

a first portion extending from said opening and which is defined by substantially flat and substantially parallel opposing walls which are spaced apart to receive said wire therebetween;

a second bottom portion adjacent said first portion and remote from said opening and defining the bottom of said notch, said second portion being generally V- or U-shaped and defined by inclined walls which are directed toward each other and toward the bottom of said notch, the inclination of said inclined walls of said second portion of said notch being such that said wire when received in said second portion is intercepted by said inclined walls near the upper portion of said inclined walls;

a third portion immediately adjacent said second bottom portion, said third portion being defined by substantially parallel opposing walls which are spaced apart a distance less than the spacing between the substantially parallel opposing walls of said first portion of said notch; and a fourth portion between said first and third portions, said fourth portion being defined by inclined walls which are directed toward each other and toward the bottom of said notch and connecting the walls of said first and third portions; and said screw member being threaded along its length at least to a position substantially where said bottom portion of said notch begins, and having a resilient quality whereby on turning at least one of said screw and nut members relative to the other so that a wire positioned through said notch is intercepted by said nut member and then forced deeper into said second portion of said notch, the angle of said inclined notch walls is increased, the wire is clamped by said members and said nut member is locked on said screw member;

whereby a wire having a dimension corresponding to the distance between the opposing walls of said first portion is caused to bear upon the inclined walls of said fourth portion to increase the angle of inclination of the walls of said fourth portion when intercepted and forced by the nut member deeper into said notch, and a wire having a dimension corresponding to the spacing between the opposing walls of said third section is caused to bear against the inclined surfaces of said second bottom portion to increase the angle of inclination thereof when said wire is intercepted by said nut member and forced deeper into said second portion of said notch.

* * * * *